(12) United States Patent
Kanda (10) Patent No.: US 7,443,491 B2
(45) Date of Patent: Oct. 28, 2008

(54) SYSTEM FOR COLLECTING INFORMATION ON BIOLOGICAL PARTICLES

(75) Inventor: Masahiko Kanda, Kobe (JP)

(73) Assignee: Bay Bioscience Kabushiki Kaisha, Hyogo (JP)

(*) Notice: Subject to any disclaimer, the term of this patent is extended or adjusted under 35 U.S.C. 154(b) by 353 days.

(21) Appl. No.: 10/537,091

(22) PCT Filed: Dec. 3, 2003

(86) PCT No.: PCT/JP03/15461

§ 371 (c)(1),
(2), (4) Date: Jan. 18, 2006

(87) PCT Pub. No.: WO2004/051238

PCT Pub. Date: Jun. 17, 2004

(65) Prior Publication Data

US 2006/0152707 A1    Jul. 13, 2006

(30) Foreign Application Priority Data

Dec. 3, 2002  (JP) .............................. 2002-351162

(51) Int. Cl.
G01N 21/00  (2006.01)
G01N 21/64  (2006.01)
G01N 15/14  (2006.01)

(52) U.S. Cl. .............................. 356/73; 356/72; 356/318
(58) Field of Classification Search .................. 356/72, 356/73
See application file for complete search history.

(56) References Cited

U.S. PATENT DOCUMENTS

| | | | |
|---|---|---|---|
| 4,498,755 A | 2/1985 | Unterleitner | |
| 4,545,677 A | 10/1985 | Chupp | |
| 4,702,598 A | * 10/1987 | Bohmer | ........................ 356/73 |
| 4,981,580 A | 1/1991 | Auer | |
| 5,489,977 A | * 2/1996 | Winslow et al. | ............... 356/73 |
| 6,133,044 A | * 10/2000 | Van den Engh | ............ 436/177 |

FOREIGN PATENT DOCUMENTS

| | | |
|---|---|---|
| EP | 0 121 262 B1 | 11/1991 |
| JP | 62-44650 A | 2/1987 |
| JP | 01-129161 | * 5/1989 |
| JP | 07-083819 A | 3/1995 |
| JP | 07-092077 A | 4/1995 |
| JP | 10-73528 A | 3/1998 |
| JP | 10-132728 A | 5/1998 |
| JP | 10-197440 A | 7/1998 |
| JP | 2002-31595 A | 1/2002 |
| JP | 2002-521658 A | 7/2002 |
| WO | WO 85/05680 | * 12/1985 |
| WO | WO 00/05566 | 3/2000 |

* cited by examiner

*Primary Examiner*—F. L Evans
(74) *Attorney, Agent, or Firm*—Harness, Dickey & Pierce, P.L.C.

(57) ABSTRACT

A system (1) for collecting biological information on a dyed biological particle (cell or chromosome) by irradiating light onto liquid containing the dyed biological particles and for detecting information light therefrom is provided according to the present invention. The system includes a path-defining structure (2) of transparent material defining a flow path (3) through which the liquid containing the dyed biological particles runs, an irradiation apparatus (5) for irradiating light onto the particles passing through the flow path (3), a first detecting apparatus (21) for detecting first information light obtained from the irradiated particle, and a second detecting apparatus (25) for detecting second information light obtained from the irradiated particle. At least one of the first and second detecting apparatuses (21, 25) includes one or more fiber optics (26, 27), of which one ends (61, 62) are arranged adjacent the flow path (3) so as to collect the information light.

19 Claims, 10 Drawing Sheets

SYSTEM FOR COLLECTING INFORMATION ON BIOLOGICAL PARTICLES

TECHNICAL FIELD

The present invention relates to a system for collecting biological information on biological particles such as cells and chromosomes. In particular, the present invention relates to a flow cytometer or a cell sorter which forms a laminar flow containing cells or chromosomes dyed with pigment material such as fluorochrome, irradiates light such as laser beam on the laminar flow to detect information light (scattered light and fluorescent light), converts optical information within the information light into electrical signals to collect biological information on cells or chromosomes, and if desired, extracts a group of particular cells or chromosomes based upon the biological information.

BACKGROUND ART

As the biotechnology has been developed, a flow cytometer is more commonly used in the fields of medicine and biology for automatic analysis and fractionation of cells or chromosomes (which are referred to simply as "cells"). The flow cytometer forms a stream of the analyte cells within a flow channel performing as cell aligning means, and irradiates laser beam on the stream of the cells to detect information light emitted/scattered at the cells (forward-scattered light, fluorescent/side-scattered light) Also, it converts the information light into electrical signals to analyze the cells based upon the electrical signals, allowing high throughput of analyzed cells and extraction (sorting) of a particular group of cells, if necessary.

Figure 12:
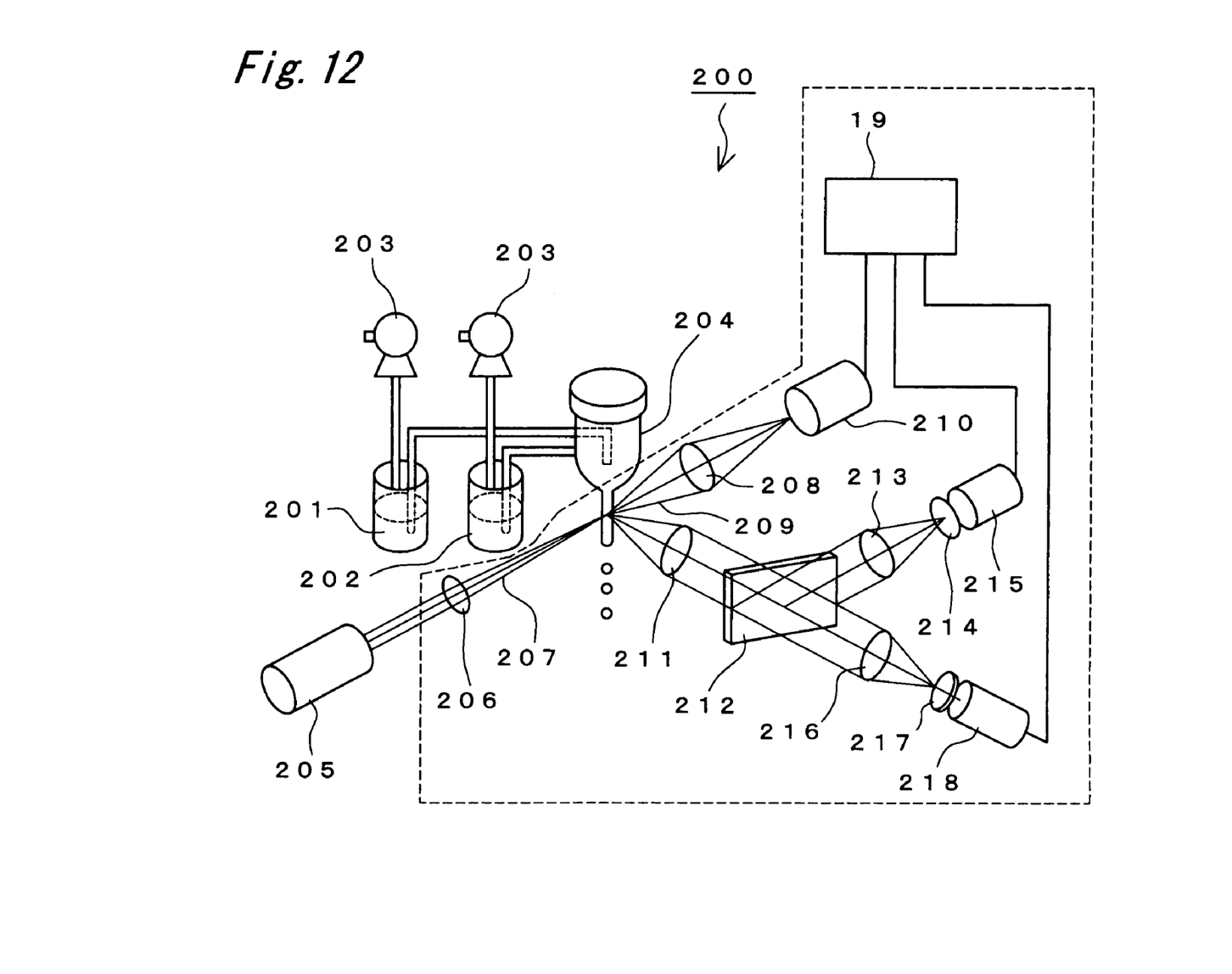
FIG. 12 is a schematic view a conventional system for collecting information on biological features of biological particles.

FIG. 12 is a schematic view of the flow cytometer, illustrating a typical structure and operation thereof. In the flow cytometer shown in the drawing, a liquid suspension 201 containing cells received in a container and a sheath fluid 202 received in another container are guided into a funnel-shaped flow chamber (nozzle) 204 by air pumps 203. In the flow chamber 204, the sheath fluid 202 forms a cylindrical laminar flow, i.e., a sheath flow, encompassing the liquid suspension 201 therein, in which a discrete one of the cells runs one-by-one along the central axis of the flow chamber 204. Where the sheath flow is faster as closer to the bottom end of the flow chamber 204, laser beam 207 is irradiated from a laser beam source 205 and focused by a collective (focusing) lens 206. Most of the cells in the liquid suspension 201 are fluorescently labeled with fluorescent material such as a fluorescent pigment and a fluorescent-labeled monoclonal antibody. Therefore, irradiation of the laser beam onto the cells causes the scattered light and the fluorescent light.

The scattered light passes through collective optics including a collective lens 208 and a beam block 209 to an optical detector 210 such as a photodiode designed for detecting the scattered light. As to the fluorescent light, red-based fluorescent light is received through another collective optics including a collective lens 211, a half-mirror 212, a collective lens 213, and a filter 214 by an optical detector 215, also green-based fluorescent light is received through the half-mirror 212, a collective lens 216 and a filter 217 by an optical detector 218. Photomultiplier tubes are typically utilized as the fluorescent detectors 215, 218 capable of detecting faint fluorescent light. A signal processing circuit 219 receives various signals output from the detector 210 for the scattered light, the detector 215 for the red-based fluorescent light and the detector 218 for the green-based fluorescent light, and analyzes strength of the scattered light and the fluorescent lights, thereby to identify the analyte cell.

As above, the conventional flow cytometer is designed such that the optical detectors 215, 218 detect the scattered light and fluorescent light that are collected by the collective optics including the collective lens 211, the half-mirror 212, the collective lens 213, and the filter 214. Also, the collective lens 211 collimates the fluorescent light scattered at each of the cells running one-by-one along the central axis of the high rate flow in the chamber. (See, for example, Japanese Laid-Open Patent Applications JPA 59-000643, JPA 59-184862, JPA 60-195436, and JPA 03-503808.) However, the particles may be stuck at the orifice of the flow chamber 204, or the flow may be disturbed or inclined. In those cases, while the flow chamber 204 has to be removed from the system and cleaned, the optical alignment (including, for example, an irradiation position and a focal length of the laser beam, a position and an angle of a nozzle, an irradiation position and a focal length of the objective lens) must be adjusted, such adjustment task is considerably cumbersome and complicated. Also, it is difficult to downsize the optics used in the system since those lens incorporated therein have a high aperture ratio.

To address the above-mentioned drawbacks, an approach for optical detection at a given flow path in the flow cell (flow chamber) has been proposed, in which the collective lens with the high aperture ratio is attached onto the flow cell, for collecting the fluorescent light from the cell. However, such a small lens cannot collimate the fluorescent light sufficiently. Also, multiple collective lens often have to be combined in many cases, therefore, improvement of sensibility cannot be expected because of air layers interposed between the adjacent lens. To this end, it was impossible to downsize the optics of the system.

DISCLOSURE OF INVENTION

One of the aspects of the present invention has a purpose to provide a flow cytometer capable of adjusting the optical axis in a simple manner, and also the flow cytometer capable of detecting the biological features of the biological particles in a more precise manner.

To achieve the purpose, a system (1) collects biological information on a dyed biological particle by irradiating light onto liquid containing the dyed biological particles and detects information light therefrom. Also, the system includes a path-defining structure (2) of transparent material defining a flow path (3) through which the liquid containing the dyed biological particles runs, an irradiation apparatus (5) for irradiating light onto the particles passing through the flow path (3), a first detecting apparatus (21) for detecting first information light obtained from the irradiated particle, and a second detecting apparatus (25) for detecting second information light obtained from the irradiated particle. At least one of the first and second detecting apparatuses (21, 25) includes one or more fiber optics (26, 27), of which one ends (61, 62) are arranged adjacent the flow path (3) so as to collect the information light.

According to the system of another aspect of the present invention for collecting the biological information on the biological particle, at least one of the first and second detecting apparatuses (21, 25) includes first and second fiber optics (26, 27), of which one ends (61, 62) are arranged adjacent the flow path (3) so as to collect the information light from the particles irradiated at the first and second positions (151, 152).

BEST MODE FOR CARRYING OUT THE INVENTION

Referring to drawings, a flow cytometry system (flow cytometer) according to the present invention will be described herein.

Figure 1:
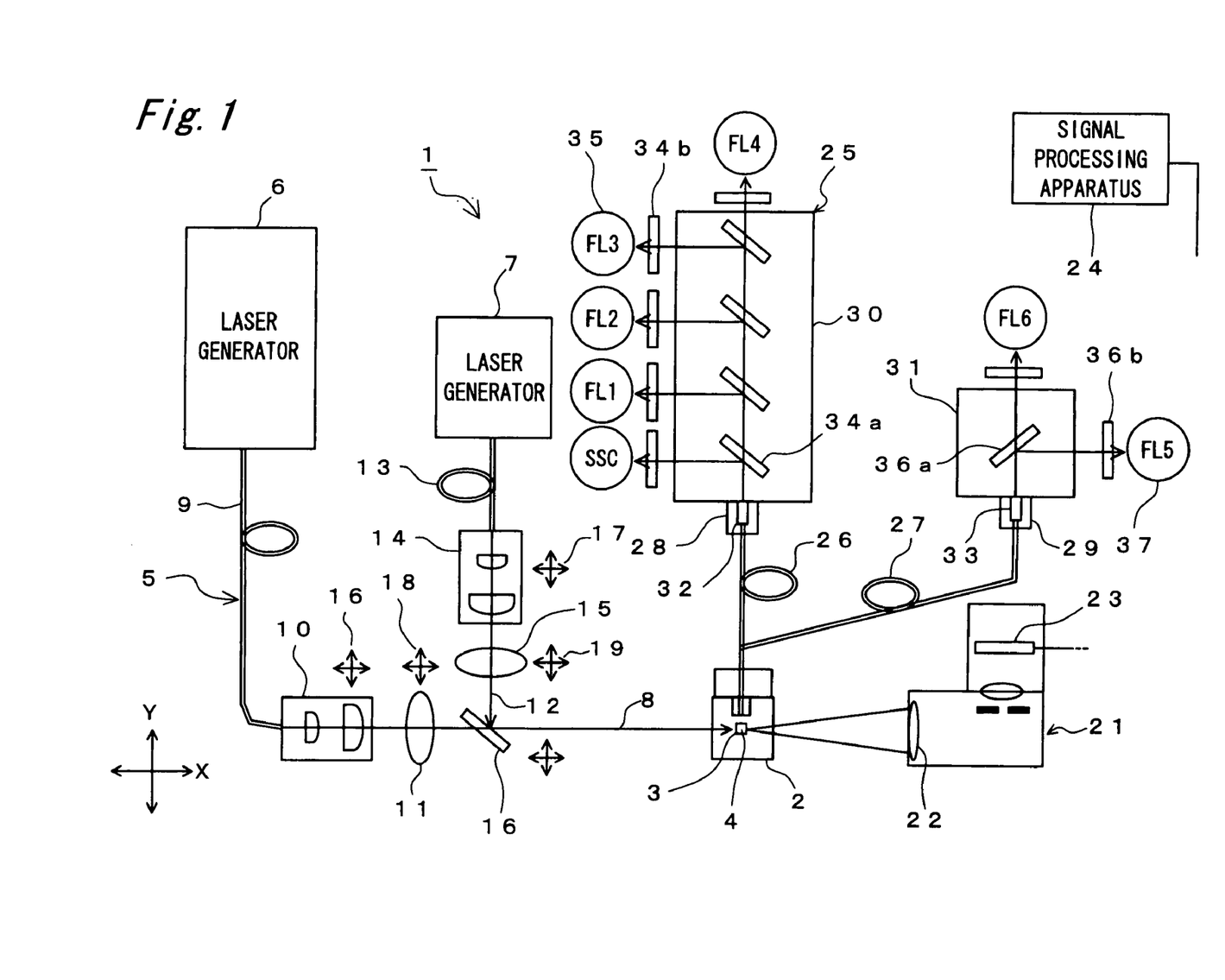
FIG. 1 is a schematic view illustrating various optical elements of a system for collecting information on biological features of biological particles according to the present invention.

I. Optical Components:

FIG. 1 illustrates several optical elements of the flow cytometer. As shown in FIG. 1, the flow cytometer 1 includes a flow-path block (path-defining structure) 2 for defining a thin flow path, through which fluid containing biological particles (cells or chromosomes) dyed with fluorescent pigment or fluorochrome antibody, typically consisting of fluid suspension containing cells and sheath fluid, runs. An irradiation apparatus 5 of the present invention includes two excitation light sources 6, 7 for irradiating light onto the sheath flow 4 running through the flow path 3 defined by the flow-path block 2. Preferably, laser-beam generators are used as the light sources for generating the laser beam having wavelengths different from each other. For instance, a first laser generator 6 is used as the first light source to generate a first laser beam having a wavelength of 488 nm (argon laser beam), and a second laser generator 7 is used as the second light source to generate a second laser beam having a wavelength of 635 nm (helium-neon laser beam). Nonetheless, other types of light sources such as a mercury lamp and a xenon lamp can be used as those light sources.

The irradiation apparatus 5 includes a fiber optics 9, a beam expander 10, and a collimator lens 11 for collecting the first laser beam 8 output from the first laser generator 6 onto substantially the center of the sheath flow 4, through the fiber optics 9, the beam expander 10, and the collimator lens 11. Also, the irradiation apparatus 5 includes a fiber optics 13, a beam expander 14, a collimator lens 15, and a mirror 16 for collecting the second laser beam 12 output from the second laser generator 7 onto substantially the center of the sheath flow 4, through the fiber optics 13, the beam expander 14, the collimator lens 15 and the mirror 16. Further, an irradiation height of "δh" is defined by a distance between the irradiation points at the sheath flow 4 of the first and second laser beams 8, 12, that is, the irradiation point of the first laser beam 8 is set above that of the second laser beam 12 by the irradiation height of "δh".

The beam expanders 10, 14 and the collimator lens 11, 15 are supported by irradiation-position adjusting devices 16, 17, 18, 19, respectively. The irradiation-position adjusting devices are designed to shift the beam expanders or the collimator lens in two (X- and Y-) directions, i.e., one is along the optical axis and the other is perpendicular to the optical axis and the sheath flow 4. The mirror 16 is supported by another irradiation-position adjusting device 20 for allowing the mirror 16 to be shifted in the X- and Y-directions and a direction perpendicular thereto.

Beyond the flow path block 2 in the direction of the incident laser beams 8, 12, a first detecting apparatus 21 is arranged for detecting the forward-scattered light scattered by the particles running through the flow path in the flow-path block 2. Similar to the detecting apparatus as described with FIG. 12, the first detecting apparatus 21 of the present invention includes a collective lens 22 and an optical detector 23 designed such that the forward-scattered light is focused by the collective lens 22 onto the optical detector 23. Also, the optical detector 23 is electrically connected with the signal processing apparatus 24 so that information detected by the optical detector 23 is transmitted to the signal processing apparatus 24 which in turn processes the information. On the other hand, a second detecting apparatus 25 is provided for detecting fluorescent/side-scattered light from the cells and includes a first fiber optics 26 for receiving fluorescent/side-scattered light of the first laser beam 8 and a second fiber optics 27 for receiving fluorescent/side-scattered light of the second laser beam 12. Also, one ends of the first and second fiber optics 26, 27 are positioned at the beam-receiving points spaced from each other by the beam-receiving height (see FIG. 5). The other ends of the first and second fiber optics 26, 27 are connected via first and second fiber connectors 28, 29 to first and second spectrometers 30, 31, respectively. Preferably, provided within the fiber connectors 28, 29 are rod lens 32, 33 or other appropriate optical lens for collimating the light that have passed through the fiber optics.

The first spectrometer 30 includes a plurality of long or short pass filters (half-mirrors) 34a splitting light from the first fiber optics 26. Each of the spectroscopic filters has a function selectively reflecting or transmitting light having a predetermined range of wavelength. In particular, the first spectrometer 30 of the present embodiment includes four spectroscopic filters 34a, namely, a first filter arranged closest to the rod lens 32 for reflecting light having wavelength less than 505 nm (i.e., transmitting light having wavelength of 505 nm or more), a second filter for reflecting light having wavelength less than 550 nm (i.e., transmitting light having wavelength of 550 nm or more), a third filter for reflecting light having wavelength less than 600 nm (i.e., transmitting light having wavelength of 600 nm or more), and a fourth filter for reflecting light having wavelength less than 730 nm (i.e., transmitting light having wavelength of 730 nm or more). Also, the first spectrometer 30 includes four band-pass filters 34b, each of which is located downstream the respective spectroscopic filter 34a for selectively transmitting light having a particular range of wavelength out of the light through the spectroscopic filter 34a. In the present embodiment, a fifth band-pass filter is further provided for selectively transmitting light having a particular range of wavelength out of the light passing through the fourth filter, thus, the first spectrometer 30 includes five band-pass filters allowing the light to be selectively transmitted. Those selectively transmitted light have center wavelength of 488 nm, 530 nm, 570 nm, 680 nm, and wavelength width of 10 nm, 40 nm, 40 nm, 30 nm, respectively. Further, the first spectrometer 30 includes a plurality of optical detectors 35 (SSC, FL1, FL2, FL3, FL4) arranged downstream the band-pass filters 34b for detecting information light (the side-scattered light and the fluorescent light corresponding to the fluorescent pigment) passing through the band-pass filters.

Meanwhile, the second spectrometer 31 includes a spectroscopic filter 36a, two of band-pass filters 36b, and two of optical detectors 37 (FL5, FL6). The spectroscopic filter 36a selectively splits light from the second fiber optics 27 by reflecting light having wavelength less than 730 nm and transmitting light having wavelength of 730 nm or more. The band-pass filters 36b each selectively transmit light having the center wavelength of 660 nm and 785 nm and the wavelength range of 30 nm and 50 nm, respectively. The optical detectors 37 each detect the information light (fluorescent light corresponding to the fluorescent pigment) passing through the band-pass filters 36b. Also, like the optical detector 23 of the first detecting apparatus 21, the detectors 37 of the second detecting apparatus are connected with the signal processing apparatus 24 so that the information obtained by the optical detectors 37 is transmitted to the signal processing apparatus 24 for further analysis.

According to the flow cytometer so structured, the first laser beam 8 generated by the first laser generator 6 passes through the fiber optics 9, the beam expander 10, and the collective lens 11 to be irradiated onto the biological particle in the sheath flow running within the flow channel 3 defined by the flow-path block 2. Also, the second laser beam 12 generated by the second laser generator 7 passes through the fiber optics 13, the beam expander 14, and the collective lens 15 so as to be irradiated onto the biological particle carried in the sheath flow running within the flow channel 3 defined by the flow-path block 2. It should be noted that the irradiation positions (heights) where the first and second laser beam 8, 12 are irradiated onto the sheath flow are different from each other.

The biological cells carried by the sheath flow 4 are dyed with fluorescent pigment or fluorescent-labeled antibody. The forward-scattered light, which is scattered forwardly in relative to the incident light, is collected by the collective lens 22 of the first detecting apparatus 21 and received by the optical detector 23. Then, the optical detector 23 reads the optical information within the forward-scattered light to convert it into electric signals. Meanwhile, the fluorescent/side-scattered light from the particle irradiated by the first laser beam 8 are received by the first fiber optics 26 of the second detecting apparatus 25 that is provided on the side in relative to the incident light. Also, the fluorescent and side-scattered light from the particle irradiated by the second laser beam 12 are received by the second fiber optics 27 of the second detecting apparatus 25. The light received by the first fiber optics 26 is transmitted via the fiber connector 28 to the first spectrometer 30, in turn split by a plurality of the spectroscopic filters 34a into a plurality of optical elements, and detected by the optical detectors 35. The optical detectors 35 (SSC, FL1, FL2, FL3, FL4) detect only light having wavelength different from one another, which have passed through the respective one of the band-pass filters 34b. Similarly, the light received by the second fiber optics 27 is transmitted via the fiber connector 29 to the second spectrometer 31, in turn split by the spectroscopic filters 34a into two of optical elements, and detected by the optical detectors 37. Thus, the wavelength ranges of the light detected by the optical detectors 37 are different from each other. As above, after detecting the fluorescent scattered light and light, the optical information within the light is converted into electrical signals that is to be forwarded to the signal processing apparatus 24. Then, the processed signals are used for identifying the biological features and for sorting the particles, as will be described below.

Figure 2:
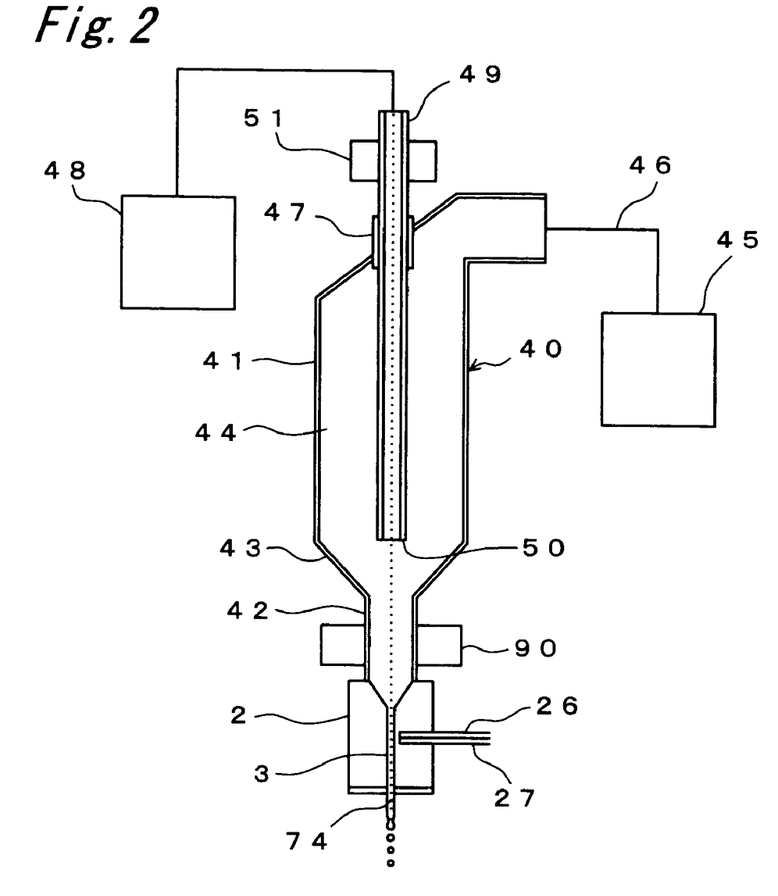
FIG. 2 is a cross sectional side view illustrating a hydrodynamic structure of the system for collecting information on biological features of biological particles according to the present invention.

II. Hydrodynamic Components:

The hydrodynamic components of the cytometer will be described herein. FIG. 2 schematically illustrates a laminar-flow generating container 40 and the flow-path block 2 connected thereto at the bottom end. The container 40 includes an upper large-diameter cylinder 41, a lower small-diameter cylinder 42, and a taper member 43 for connection between the large-diameter cylinder 41 and the small-diameter cylinder 42, which are all concentrically arranged, defining a laminar-flow generating chamber 44. The top end of the container 40 is connected to the sheath-fluid source 45 via a sheath-fluid line 46. A tube capsule 47 is fixed on the ceiling of the container 40, which extends along the central axis of the container 40. Also, a suspension-fluid tube 49 connected with the suspension-fluid source 48 is inserted into the tube capsule 47. The inner diameter of the tube capsule 47 and the outer diameter of the suspension-fluid tube 49 are selected such that the suspension-fluid tube 49 can be slid along the tube capsule 47 and slightly inclined in relative to the tube capsule 47. Thus, while a nominal gap is defined between the tube capsule 47 and the suspension-fluid tube 49, an appropriate sealing member such as an O-ring made of rubber is filled up with the gap.

Figure 3:
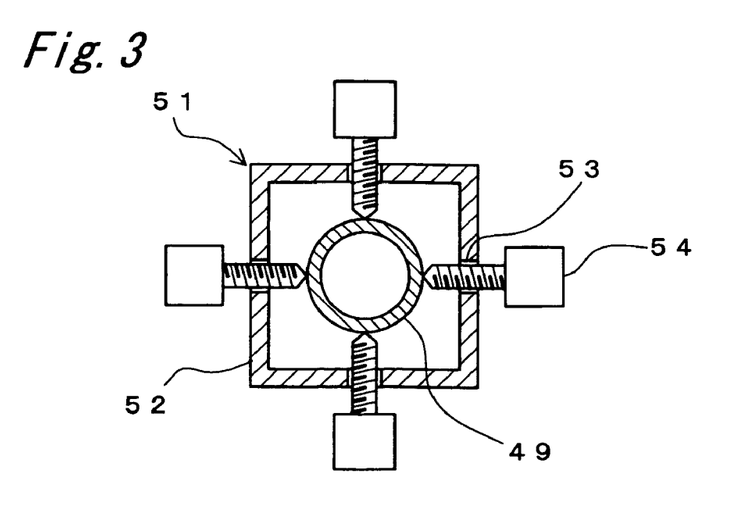
FIG. 3 is a cross sectional view of an angle adjusting device incorporated in the system of FIG. 2.

In order to adjust the position of a suspension-fluid outlet 50 of the suspension-fluid tube 49, an upper portion of the suspension-fluid tube 49 is connected with an angle adjusting device 51, which is supported by the container 40 or a platform (not shown) also supporting the container 40. Although various inclining mechanisms can be adapted to the angle adjusting device 51, one example for the inclining mechanism is illustrated in FIG. 3. The suspension-fluid tube 49 is surrounded and centered within a square-shaped frame 52 by adjusting a plurality of screws 54 on the frame 52, two pairs of which sandwich the suspension-fluid tube 49, as can be seen in FIG. 3. The screw-based angle adjusting mechanism can perform the function also as an alignment member for the vertical position of the suspension-fluid tube 49, in conjunction with the sealing member disposed in the gap between the tube capsule 47 and the suspension-fluid tube 49.

The flow-path block 2 connected to the bottom end of the container 40 is made of transparent material selected from a group consisting of quartz, glass, fused silica, transparent plastic, etc. Also, the flow-path block 2 has a thin path flow 3 concentrically arranged with the central axis of the container 40. The flow-path block 2 defining the path flow 3 has a rectangular cross section including longer member walls 55, 56 extending along the X-direction and shorter member walls 57, 58 extending along the Y-direction as shown in FIG. 4.

Also, the flow-path block 2 is designed such that the first and second laser beams 8, 12 entering from one of the shorter member wall 57 cause the forward-scattered light to be output through the opposing shorter member wall 58 and the fluorescent/side-scattered light to be output through one of the longer member wall 56.

Figure 4:
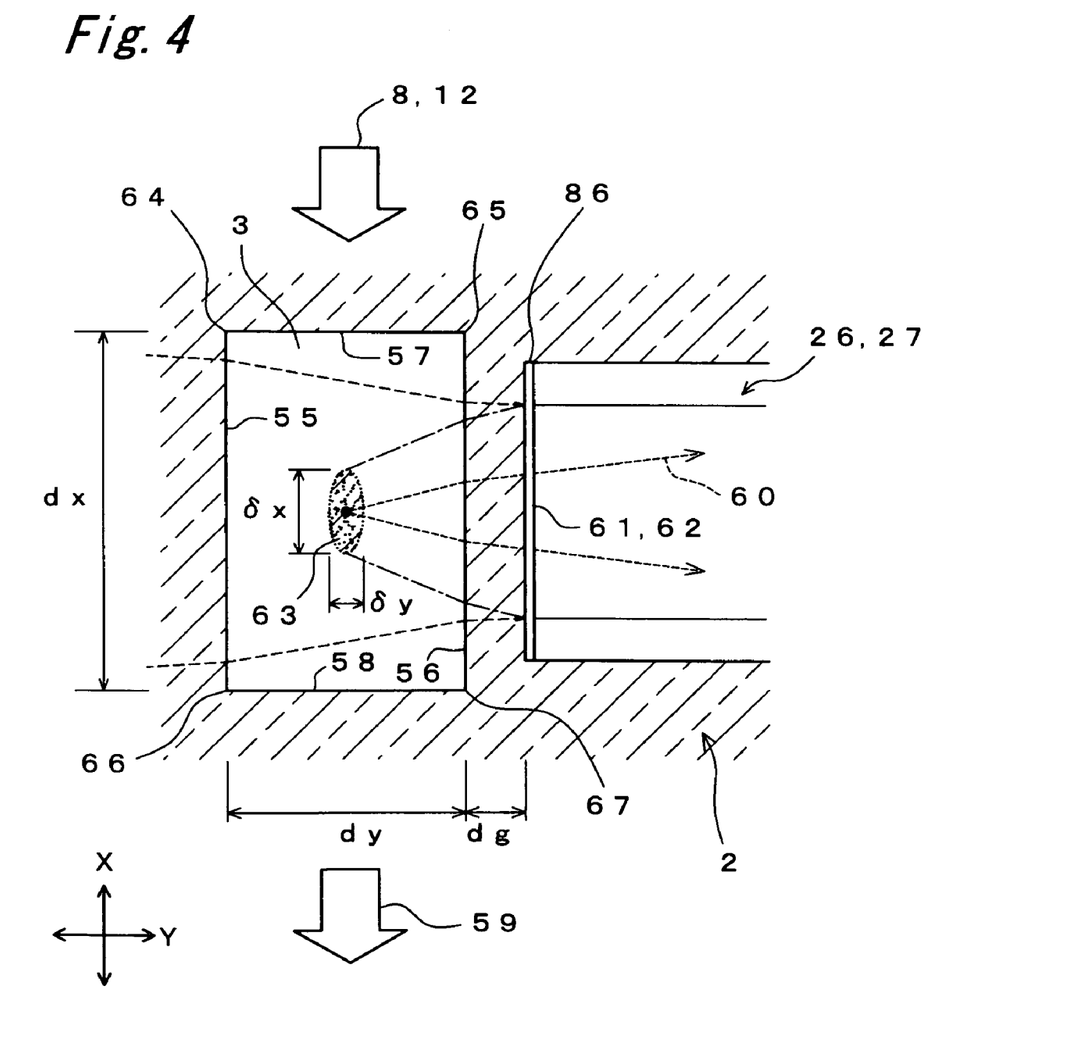
FIG. 4 is an enlarged cross sectional view of a detection flow path of the system of FIG. 1 and a portion of fiber optics arranged adjacent thereto.
Figure 5:
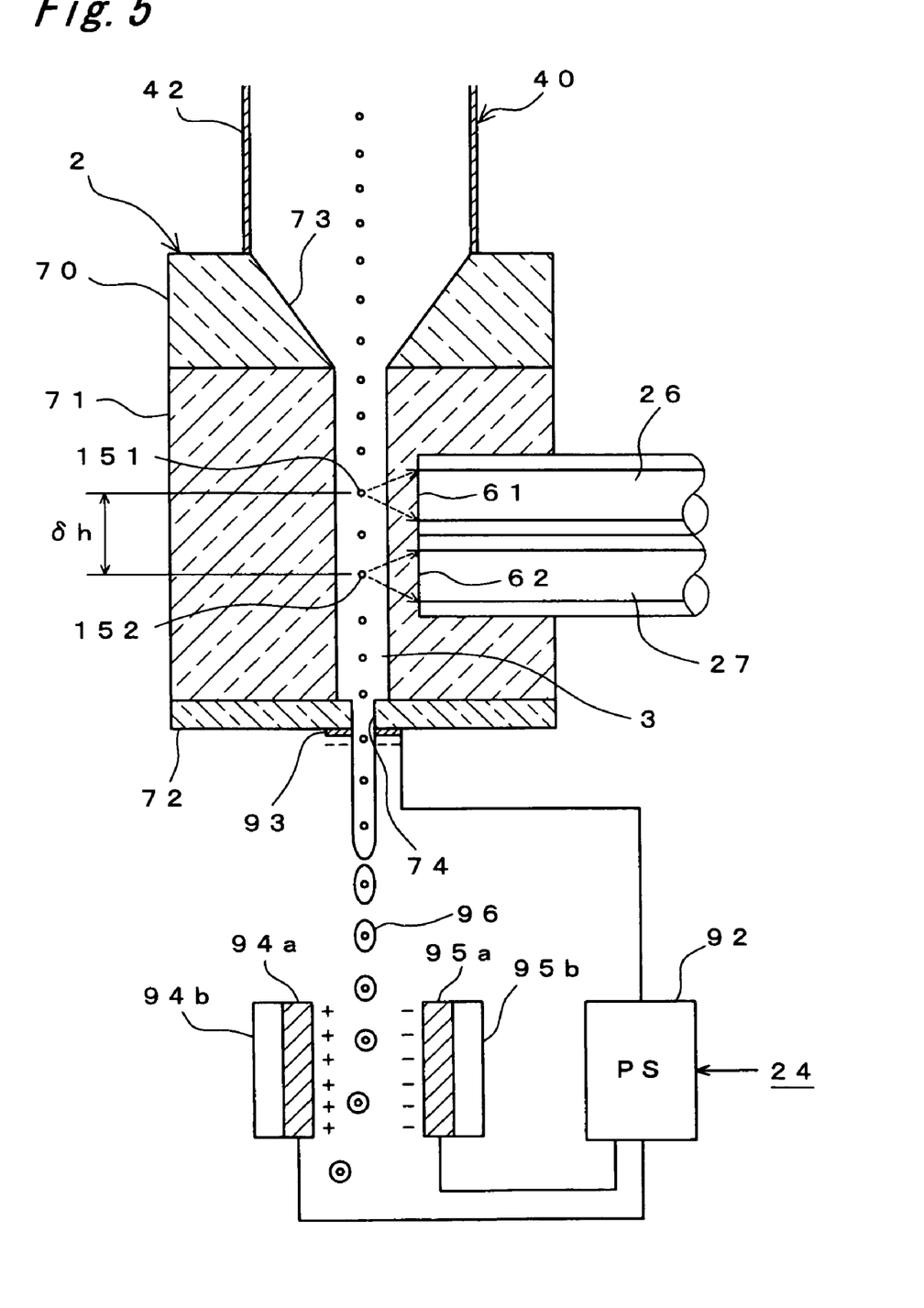
FIG. 5 is an enlarged cross sectional view of a detection flow path of the system of FIG. 1 and a portion of fiber optics arranged adjacent thereto.

As shown in the enlarged views of FIGS. 4, 5, the flow-path block 2 supports the first and second fiber optics 26, 27 for detecting the fluorescent/side-scattered light. Each of the fiber optics has a core for guiding light and a cladding layer surrounding the core, similar to a typical one of fiber optics. One ends of the first and second fiber optics 26, 27 are formed as being oriented in a direction perpendicular to the central axis of the fiber optics. Also, one ends of the first and second fiber optics 26, 27 are spaced away from the longer member wall 56 by a predetermined gap "dg" as shown in FIG. 4, and arranged facing along the horizontal direction (Y-direction) perpendicular to the central axis of the container. As illustrated in FIG. 5, the first and second fiber optics 26, 27 are aligned along the central axis of the container so that the center points of the first and second fiber optics 26, 27 are set at the same level of the irradiation points 151, 152 of the first and second laser beams 8, 12, respectively.

As illustrated in FIG. 4, the size of the flow path (i.e., dimension "dx", "dy") and the distance between the one ends of the fiber optics and the longer member wall 56 are determined, taking consideration of the core diameter "df" and aperture ratio "NA", securing two conditions to be met. That is, the light from the oval region 63 through which the cells possibly run in the flow path 3 should essentially enter into the core, and the light reflected or scattered at the corner portions 64-67 of the flow path 3 should not enter into the core. Satisfying the above conditions allows the fluorescent/side-scattered light to be entered into the fiber optics 26, 27 and eliminates the noise due to the reflected or scattered light at the corner portions, from the detected results. These conditions can be met if the dimensions δx, δy of the region 63 are in the range of approximately ¼ through ¹⁄₁₀ of the sizes dx, dy of the flow path 3. As one example, the flow path 3 is configured to have the sizes dx=200 µm, dy=100 µm.

Next, the processes for manufacturing the flow-path block 2 and for securing the fiber optics onto the flow-path block 2 will be described herein. As illustrated in FIG. 5, the flow-path block (path-defining structure) 2 includes an upper block 70 attached to the lower small-diameter cylinder 42 of the container 40, a lower block 71 attached to the bottom portion of the upper block 70, and an orifice plate attached to the bottom end of the lower block 71. Those components are attached by means of adhesive or heat for heat-sealing. The upper block 70 has a tapered flow path 73 narrowing the cross section along a downward direction for connecting the small-diameter cylinder 42 with the flow path 3. The flow path 3 is defined within the lower block 71. Also, the orifice plate 72 has a flow path (orifice) 74 narrower than one of the flow path 3.

Figure 6:
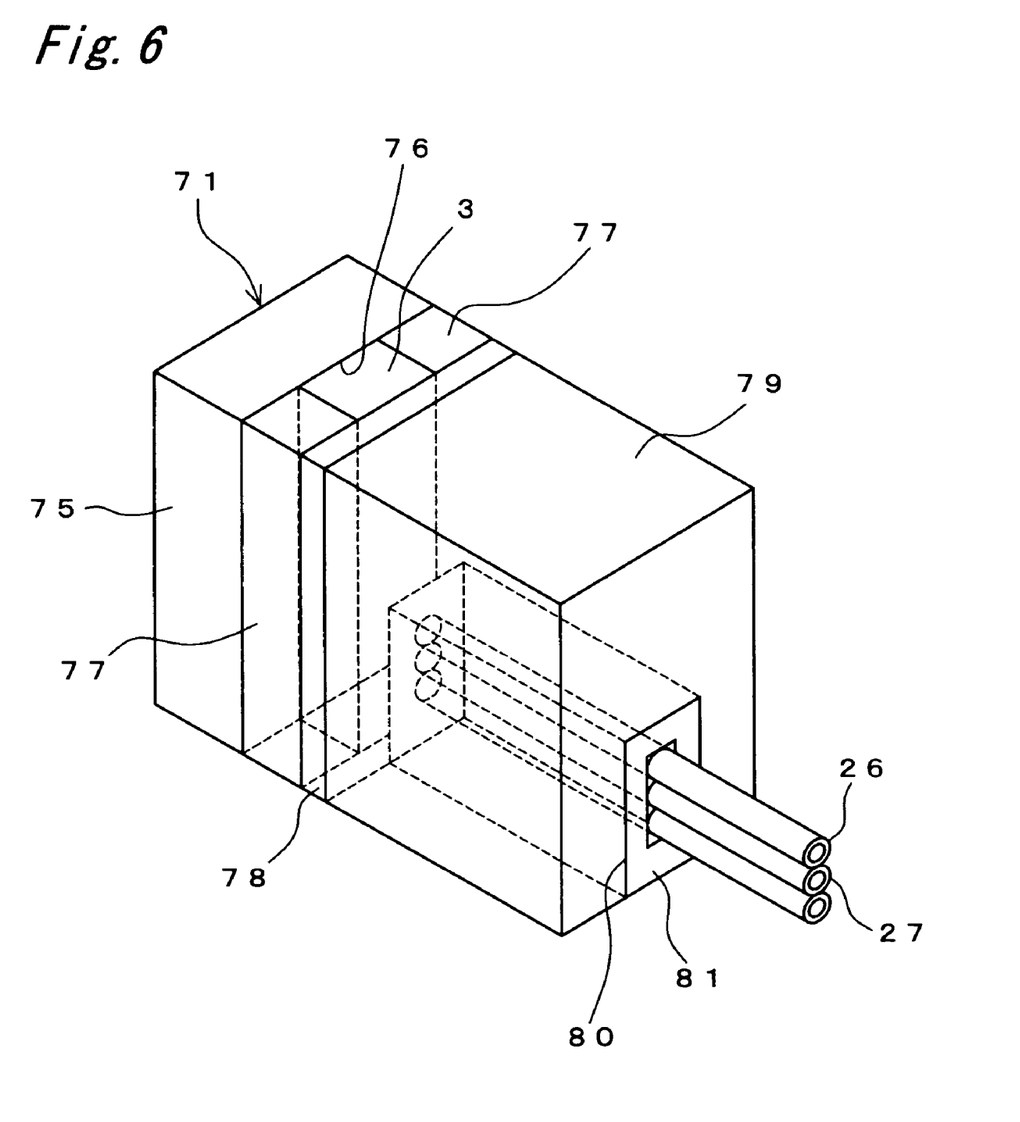
FIG. 6 is an enlarged perspective view of a path-defining member (flow-path block) of the system of FIG. 1.

The lower block 71 is formed by combining a plurality of submembers. For instance, as shown in FIG. 6, a plate 75 is provided, and a pair of spacing plate 77 spaced from each other by a distance that corresponds to the distance dx between longer member walls are arranged and secured to the plate 75. Then, a cover plate (partition wall) 78 having a predetermined thickness dg is secured on both of the spacing plates 77, and finally a holder block 79 is arranged and secured on the cover plate 78.

Figures 7A, 7B:
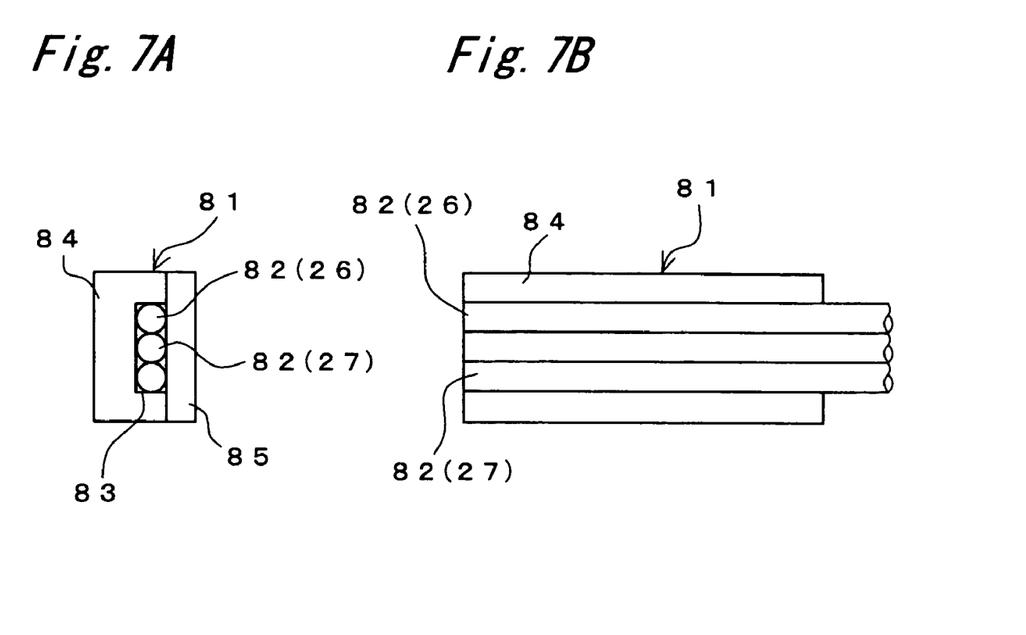
FIG. 7A is an enlarged elevational view of a fiber holder incorporated in the path-defining member of FIG. 6.
FIG. 7B is an enlarged side view of a fiber holder incorporated in the path-defining member of FIG. 6.

The holder block 79 has one surface facing the cover plate 78 and another surface opposing thereto, and includes a concave portion 80 extending through both of the surfaces, in which a fiber holder 81 is inserted and fixed. As illustrated in FIGS. 7A and 7B, the fiber holder 81 includes a bracket-shaped first block 84 having a gutter (fiber-receiving chamber) 83 for receiving and arranging a plurality of fiber optics 82 in parallel, and a plate-shaped second block 85 for covering the gutter 83. The size of the first and second blocks is configured so that the fiber holder 81 formed by combining the first and second blocks 84, 85 is outlined as being congruent with the concave portion. The gutter 83 is formed such that a plurality of the fiber optics (including at least first and second fiber optics 26, 27) can be arranged in parallel with gaps between those fiber optics as small as possible. The fiber holder 81 with the fiber optics received in the gutter 83 is inserted and secured in the concave portion 80 of the holder block 79. If necessary, those fiber optics 82 are bonded in the fiber holder 81 with adhesive.

In order to measure the fluorescent light at high is accuracy, preferably, there is no air between one end of the fiber optics 26, 27 and the cover plate 78. Thus, it is desirable to fill up the gap therebetween with filler material 86 such as transparent adhesive, oil, and gel (see FIG. 4). Also, it is desirable that the cover plate 78 is made of material having refraction index that is substantially the same as the fiber optics (especially, core), or that is substantially intermediate between the fiber optics 26, 27 and the cover plate 78. This allows the fluorescent light and scattered light to be collected in an efficient manner.

Figure 8A:
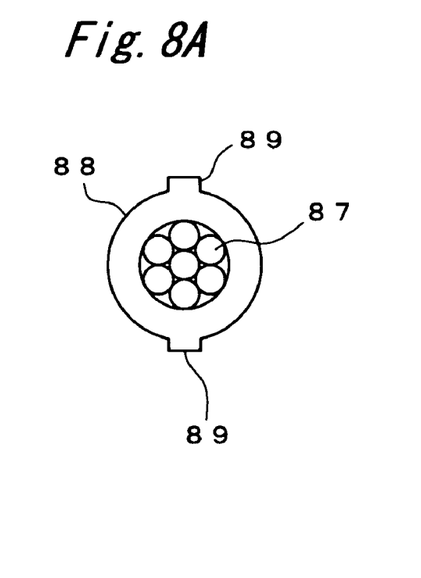
FIG. 8A is an enlarged elevational view of the fiber holder with a fiber bundle.
Figure 8B:
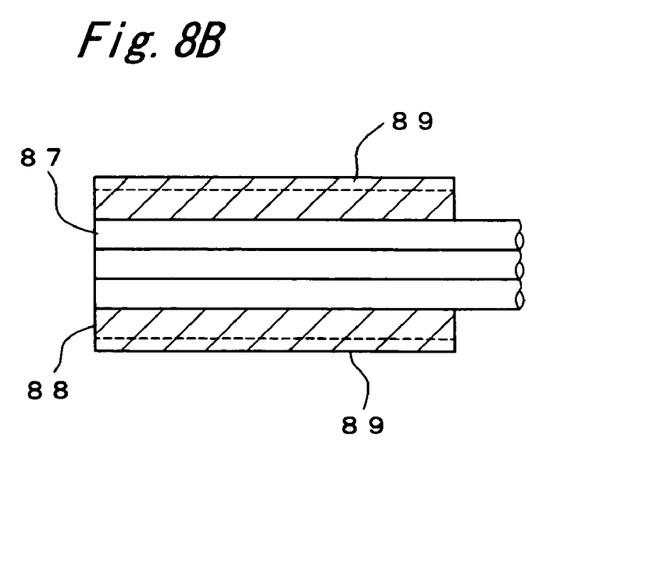
FIG. 8B is an enlarged cross sectional view of the fiber holder shown in FIG. 8A.

While a plurality of fiber optics 82 are received within the gutter 83 in the above embodiment, a cylindrical fiber holder 88 may be used for receiving a fiber bundle that is formed by a central fiber optics and six surrounding fiber optics. In this case, only two of seven fiber optics may be used as the first an second fiber optics 26, 27. Also, in the present embodiment, preferably, the cylindrical fiber holder 88 has a boss (or a dent) formed on the circumference thereof and the holder block 79 has a corresponding dent (or boss, not shown) so as to prevent rotation of the fiber holder 88 in the holder block 79.

Referring back to FIG. 2, an oscillating device 90 is provided on a circumference of the small-diameter cylinder 42 for imparting oscillation on the fluid flow containing cells from the circumference towards the inside thereof, so that the fluid flow is split into a plurality of droplets containing cells, each of which droplet is ejected (generated) from the bottom orifice 74 of the flow-path block 2. Preferably, a plurality of the oscillating devices 90 are symmetrically arranged around the small-diameter cylinder 42. Also, it is preferable that a piezo-actuator (PZT) is used as the oscillating device 90.

The flow cytometer 1 includes a sorting apparatus 91 beneath the flow-path block 2 for sampling particular groups of particles. The sorting apparatus 91 includes a power supply circuitry 92, an electrode 93 contacting with the fluid flow that is to be ejected from the orifice 74, a pair of conductive electrode plates (deflection plate) 94a, 95a provided beneath the orifice 74, allowing the ejected flow to pass through between the electrode plates. It should be noted that the electrode 93 may be provided at any non-limited positions as long as it contacts with the fluid running through the flow-path in the flow-path block 2. The distribution of the electric field between the electrode plates 94a, 95a may change when moisture is attached on the electrode plates 94a, 95a. To prevent this, the electrode plates 94a, 95a are made of porous metal plate, and a pair of aspiration devices 94b, 95b are resided on the rear side of the electrode plates. Thus, charged fluid particles adhered on the electrode plates 94a, 95a are driven through the holes in the electrode plates 94a, 95a to the rear side thereof. Therefore, the electric field formed between the electrode plates 94a, 95a can be kept in a stable condition.

According to the structure as above, the sheath fluid supplied from the sheath-fluid source 45 moves downwardly inside the container 40, as shown in FIG. 2. The amount of the sheath fluid supplied per unit time is determined so that the sheath flow moves in a laminar flow around the central axis of the container 40. In the meanwhile, the suspension fluid supplied from the suspension-fluid source 48 is guided via the suspension-fluid tube 49 to the center of the sheath flow running as the laminar flow. This allows the sheath flow in the cylindrical laminar flow to surround the suspension fluid and to encompass each of particles running one-by-one through the central axis of the container 40 in a precise and discrete manner. Then, the suspension fluid and the sheath fluid are accelerated in the taper member 43 to the small-diameter cylinder 42, and again accelerated in the tapered flow path 73 of the flow-path block 2 to the flow path 3.

As illustrated in FIG. 4, when the first and second laser beams 8, 12 are irradiated onto the particles passing through the flow path 3, the forward-scattered light 59 and the fluorescent/side-scattered light 60 emanate from the particles. The forward-scattered light 59 pass through the wall surface 58 in the direction same as those of the first and second laser beams 8, 12, and detected by the first detecting apparatus 21. Also, the fluorescent/side-scattered light 60 of the first and second laser beams 8, 12, are collected into the first and second fiber optics 26, 27, and detected by the second detecting apparatus 25. The noise contained in the fluorescent/side-scattered light 60 can be minimized, since the first and second fiber optics 26, 27 do not receive the light reflected at the corners 64-67 of the flow path 3. The electrical signals of the biological features for the particles obtained by the first and second detecting apparatuses 21, 25 are transmitted to the power source 92 (see FIG. 5).

The sheath fluid passing through the flow path 3 is jetted from the orifice 74. The oscillation imparted from the oscillating apparatus 90 to the small-diameter cylinder 42 of the container 40 causes the jetted sheath fluid to be a plurality of droplets, each of which contains the particle. In particular, according to the present embodiment, since the oscillating apparatus 90 is provided on the small-diameter cylinder 42 of the container 40, the oscillation generated by the oscillating apparatus 90 is efficiently transmitted to the mixed laminar flow thereby to properly individualize the laminar flow into a plurality of the droplets 96.

Each of the droplets 96 ejected from the orifice 74 is charged with positive or negative polarity by the electrode 93, of which potential is applied by the power supply circuitry 92. Thus, the power supply circuitry 92 controls to selectively charge a particular type of particles based upon the signals prepared with the biological features of the particles detected by the signal processing apparatus 24. The charged particles 96 are deflected when passing between the electrode plates 94a, 95a, so that only the particular sort of particles are retrieved. Liquid attached on the electrode plates 94a, 95a are aspirated through the electrode plates 94a, 95a of porous material from the aspiration devices 94b, 95b. Therefore, the constant electric field is secured between the electrode plates 94a, 95a.

If the container 40 or the flow-path block 2 is stack with the cells, the container 40 and the flow-path block 2 are removed from the platform to clean the sticking cells. After cleaning, the container 40 and the flow-path block 2 is re-installed back to the original. Since the irradiation position of the excited beams is to be arranged at the center of the flow path of the flow-path block 2, the irradiation-position adjusting devices for the beam expanders and the collective lens and as well as for the first and second laser beams are adjusted. However, since the fiber optics for detecting fluorescent/side-scattered light are secured within the flow-path block 2, adjustment of the fiber optics is not required.

Figure 9:
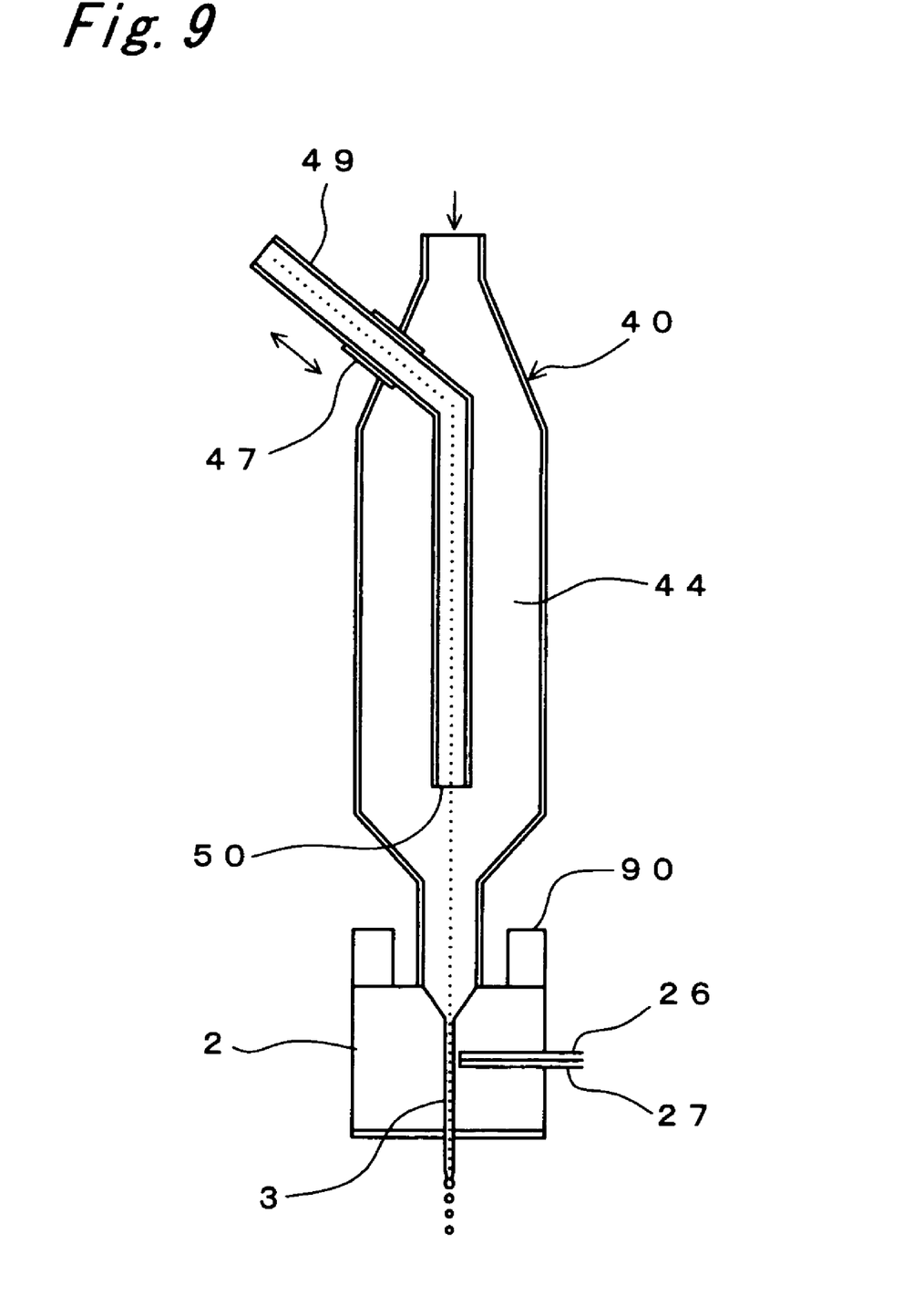
FIG. 9 is a cross sectional side view of the system of another embodiment according to the present invention.

In the foregoing embodiment, the oscillating apparatus 90 is attached on the small-diameter cylinder 42 of the container to impart oscillation on the mixed laminar flow running though the mall-diameter cylinder 42. However, as illustrated in FIG. 9, the oscillating apparatus 90 may be installed on the upper portion of the flow-path block 2 to provide vertical oscillation (along the direction of the droplets to be ejected). In this instance, the droplets are efficiently generated and shapely broken off to one another. The technique for the installation position and the oscillation direction of the oscillating apparatus 90 can be applied not only to the flow cyrometer of the present invention but also to any types of conventional flow cyrometers.

Figure 10:
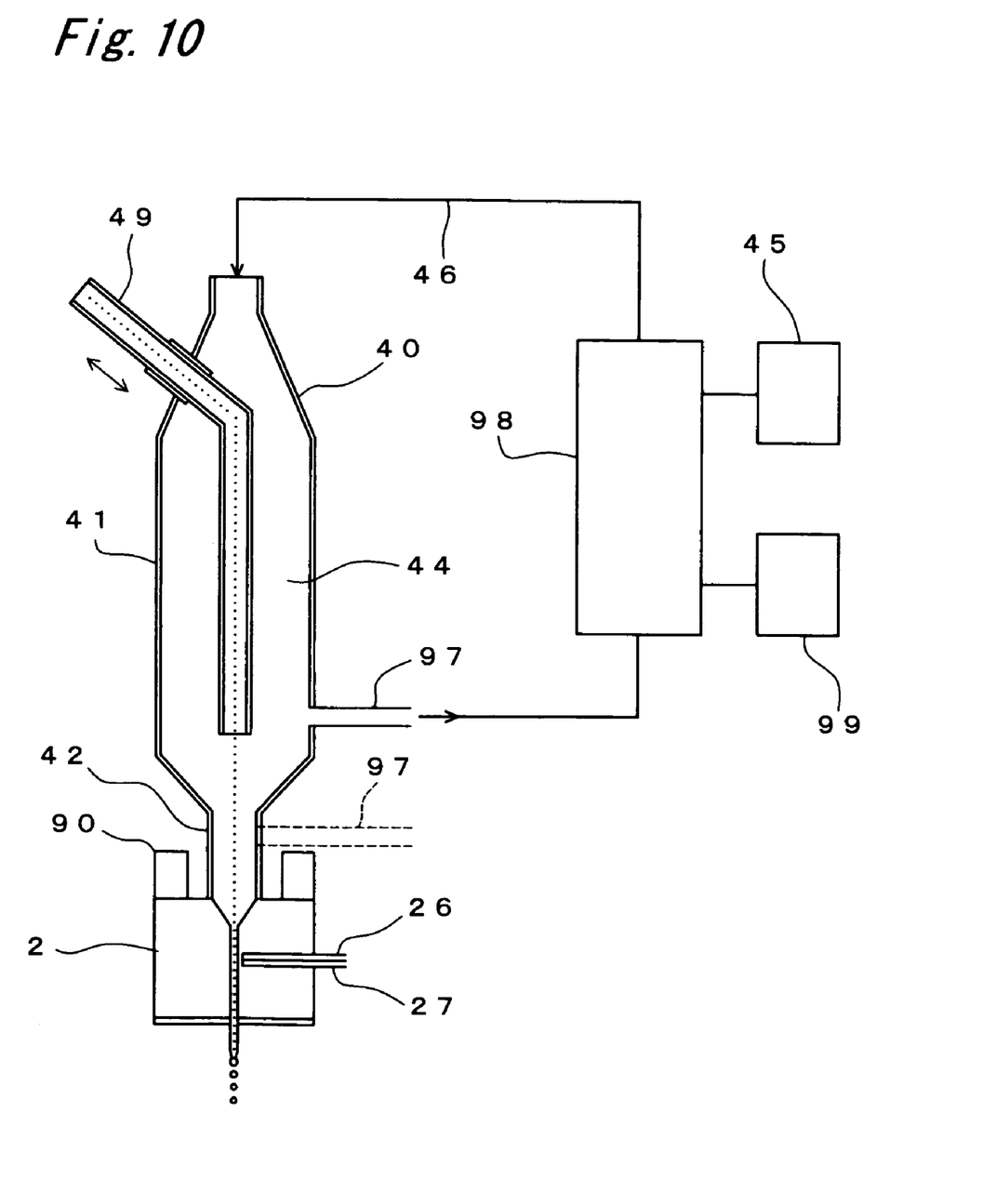
FIG. 10 is a cross sectional side view of the system of another embodiment according to the present invention, illustrating a fluidic circuit for removing debris from the sheath fluid.

Further, although in the foregoing embodiment, the suspension-fluid tube 49 is provided, which straightly extends along the central axis of the container 40, as shown in FIG. 10, another suspension-fluid tube may be used, which has an upper straight portion bent in relative to the central axis of the container 40, and a lower straight portion aligned in parallel to the central axis of the container. The supplying position of the suspension fluid from the suspension-fluid tube 49 can be adjusted by controlling insertion of the upper straight portion into the container 40. The mechanism for adjustment of the supplying position of the suspension fluid can be applied not only to the flow cyrometer of the present invention but also to any types of conventional flow cyrometers.

As illustrated in FIG. 10, a drain line 97 may be provided on at least one of the large-diameter cylinder 41 and the small-diameter cylinder 42 for draining the sheath fluid. Also, a valve mechanism 98 may be used for connection of the sheath-fluid line 46 and the drain line 97 with a sheath-fluid supply 45 and a sheath-fluid waste 99. In operation, the valve mechanism 98 is activated to selectively connect the sheath-fluid line 46 with the sheath-fluid supply 45 and the sheath-fluid waste 99 and/or to selectively connect the drain line 97 with the sheath-fluid supply 45 and the sheath-fluid waste 99. In the present embodiment, by actuating the valve mechanism 98, cells, debris, and air (bubbling) resident in the container 40 can be retrieved, and the sheath fluid in the container 40 can be exchanged in a readily manner. The structure of the lines for retrieving the cells belongs to the technique that can be applied not only to the flow cyrometer of the present invention but also to any types of conventional flow cyrometers.

Figure 11:
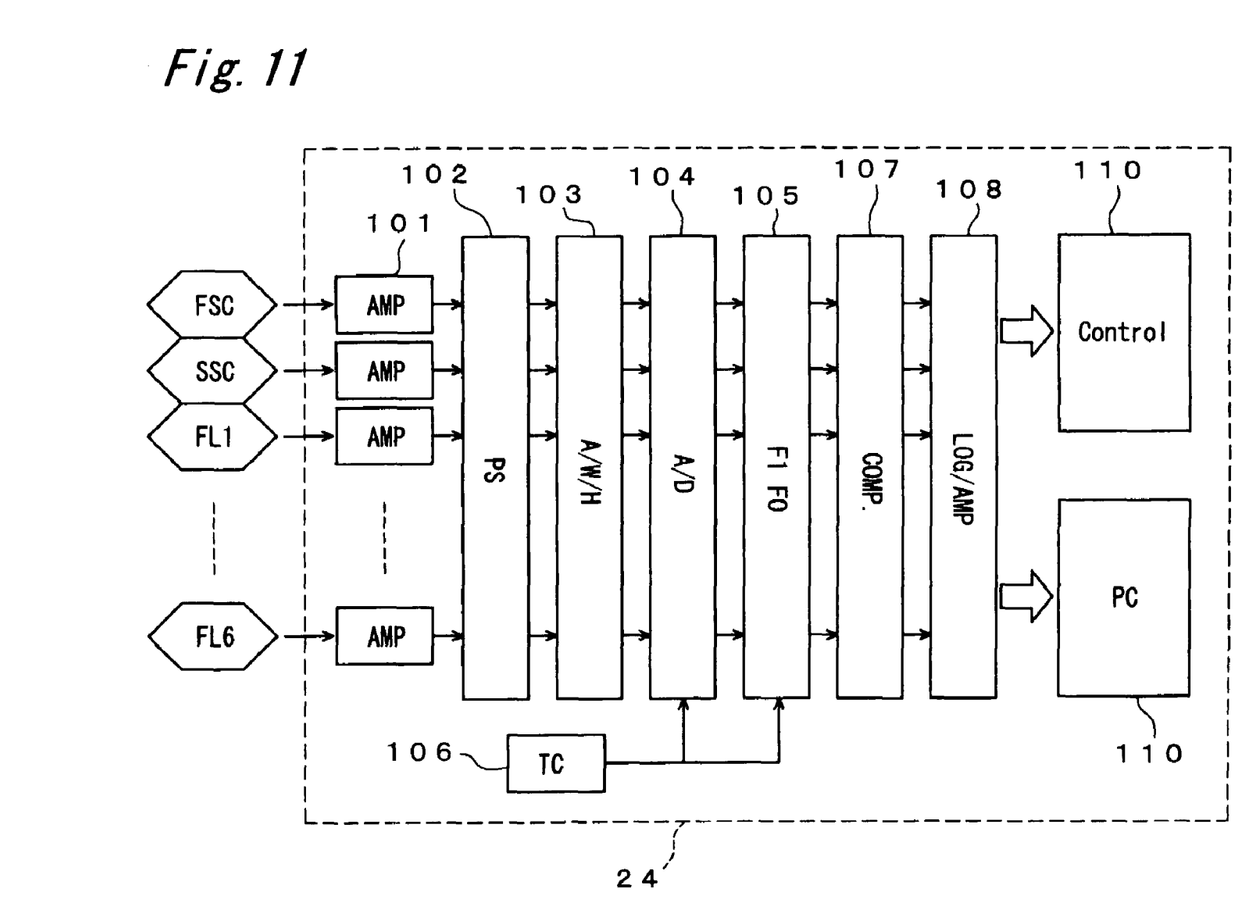
FIG. 11 is circuit diagram of a signal processing apparatus.

III. Signal Processing System:

FIG. 11 illustrates a circuit diagram of the signal processing apparatus 24, which includes a plurality of amplifiers 101 for amplifying signals (i.e., signals for the forward-scattered light, the side-scattered light, and the fluorescent light) detected by the optical detectors of the first and second detecting apparatuses 21, 25. The amplified signals are transmitted to a parameter selector (PS) 102, and are retrieved as pulse-waved signals in the predetermined wavelength range. The retrieved signals in the parameter selector 102, while still being analog signals, are transmitted to the A/W/H calculator 103 for calculating an area, width, and height of the signals. The analog signals are converted by an A/D converter 104 to the digital signals, which in turn are transmitted to and stored in a first-in first-out (FIFO) memory 105.

As above, two of the fiber optics 26, 27 of the second detecting apparatus 25 are arranged at positions different from each other along the fluid flow running through the flow path 3. Therefore, there is a time lug between the times when the second fiber optical 27 detects the fluorescent/side-scattered light from a given particle and when the first fiber optical 27 detects the fluorescent/side-scattered light from the same particle. Thus, there is time gap between the times when the signal associated with the first fiber optical 26 is input into the FIFO memory and when the signal associated with the second fiber optical 27 is input into the FIFO memory 105. The FIFO memory 105, which is connected to a timing controller 106 for determining the time lug, simultaneously outputs the signals for the given particle, taking account of the signal from the timing controller 106.

The digital signals output from the FIFO memory 105 are transmitted to a compensation circuitry (COMP) 107, in which one of the fluorescent components that is expected to be included within another one of the fluorescent components is deducted from the latter one, based upon the predetermined ratio. The compensated digital signal is transmitted to a log-converting amplifier 108 for logarithmical conversion or amplification. The converted or amplified digital signal is transmitted both into a host computer 109 and a sorting controller 110. The host computer 109 uses the signal to determine the biological features of the particles. Also, the sorting controller 110 uses the signal for controlling the power supply circuitry of the sorting apparatus.

As above, since the A/W/H calculator 103 of the signal processing apparatus 24 calculates an area, width, and height of the analog signal output from the parameter selector 102, the resolution/accuracy can be improved over the case where the A/W/H calculator is provided between the compensation circuitry and log-converting amplifier in the digital signal processor. Also, in case where the analog signal output from the amplifier is logarithmically converted and the digital signal output from the FIFO memory is compensated by the compensation circuitry for further calculating the area or the like with the A/W/H calculator, the accuracy of the logarithmic conversion for the analog signal would be poor and the compensated digital signal should be logarithmically converted and again logarithmically converted. However, the above-mentioned signal processing apparatus advantageously eliminates such drawbacks.

In the flow cytometer of the present invention as described above, while the fiber optics is used for collecting the fluorescent/side-scattered light, another fiber optics may be used for collecting the forward-scattered light. In this instance, the fiber optics for collecting the forward-scattered light may be secured adjacent the flow path in a similar manner as described with reference to FIG. 6. Also, as to the irradiation apparatus, instead of the optical elements such as the collective lens, the fiber optics may be used for guiding the laser beams from the laser generators to the flow path. In this instance, the output end of the fiber optics is preferably formed with a convex configuration for collecting the light output from the fiber optics. If so structured, the task of the optical alignment after cleaning is further reduced or eliminated.

In the above-described flow cytometer, while the first and second fiber optics for detecting the fluorescent/side-scattered light are arranged on one side of the flow path, each one of them may separately be provided on both sides of the flow path, respectively, sandwiching the flow path.

As can be seen from the above description, the optical alignment of the flow cytometer of the present invention can be made in a simple and readily manner. Also, the flow cytometer of the present invention can be used for determining the biological features in a precise manner.

The invention claimed is:

1. A system for collecting biological information on a dyed biological particle by irradiating light onto liquid containing the dyed biological particles and detecting information light therefrom, the system comprising:
   a path-defining structure of transparent material defining a flow path through which the liquid containing the dyed biological particles runs;
   an irradiation apparatus for irradiating light onto the particles passing through the flow path;
   a first detecting apparatus for detecting first information light obtained from the irradiated particle;
   a second detecting apparatus for detecting second information light obtained from the irradiated particle;
   wherein at least one of said first and second detecting apparatuses includes one or more fiber optics, of which one ends are arranged adjacent the flow path so as to collect the information light;
   a cylindrical container having a laminar-flow generating chamber provided upstream the flow path;
   a sheath-fluid line for supplying sheath fluid constituting a main body of the liquid from an upper end of the cylindrical container;
   a suspension-fluid tube arranged along the central axis of the cylindrical container for supplying suspension fluid containing the particles into the sheath fluid running within the laminar-flow generating chamber; and
   a mechanism for adjusting at least one of a position and an angle of a suspension-fluid outlet of the suspension-fluid tube.

2. The system according to claim 1,
   wherein the flow path defined by said path-defining structure has a rectangular cross section defined by a pair of first walls and a pair of second walls perpendicular to the first walls;
   wherein said irradiation apparatus emits light to one of the first walls;
   wherein said first detecting apparatus detects light transmitting through another one of the first walls; and
   wherein said second detecting apparatus detects light transmitting through one of the second walls.

3. The system according to claim 2,
   wherein one ends of the fiber optics are arranged substantially in parallel to one of the second walls.

4. The system according to claim 2,
   wherein the flow path having the rectangular cross section is designed such that light diffused and scattered at the corner portions formed at intersections of the first walls and the second walls are prevented from entering into fiber optics.

5. The system according to claim 1, said path-defining structure including:
   a first transparent member having at least one planar surface;
   a second transparent member having a pair of opposing planar surfaces in parallel to each other, one of the surfaces opposing to the first transparent member and being spaced from the first transparent member by a predetermined distance; and
   a pair of third transparent members sandwiched between the planar surface of the first transparent member and one of the surfaces opposing to the first transparent member, the pair of the third transparent members being spaced from each other by a predetermined distance, so as to define the rectangular flow path in conjunction with the first and second transparent members.

6. The system according to claim 5,
wherein said path-defining structure further includes a fourth member opposing to another one of the surfaces of the second member, for holding a fiber block therein, which supports one ends of the first and second fiber optics.

7. The system according to claim 1,
wherein at least one of said first and second detecting apparatuses includes a fiber connector at another end of the first and second fiber optics; and
wherein a collimating lens is provided within the fiber optics for collimating light that has been transmitted through the fiber optics.

8. The system according to claim 1,
wherein at least one of said first and second detecting apparatus includes a spectrometer for splitting light components from light received by the fiber optics, and a plurality of optical detectors for reading information within the light split by the spectrometer.

9. The system according to claim 1, further including:
means for imparting oscillation on the liquid in a direction perpendicular to the fluid flow.

10. The system according to claim 1, further including:
means for imparting oscillation on the liquid in a direction along the fluid flow.

11. A system for collecting biological information on a dyed biological particle by irradiating light onto liquid containing the dyed biological particles and detecting information light therefrom, the system comprising:
a path-defining structure of transparent material defining a flow path through which the liquid containing the dyed biological particles runs;
an irradiation apparatus for irradiating light onto the particles passing through the flow path;
a first detecting apparatus for detecting first information light obtained from the irradiated particle; and
a second detecting apparatus for detecting second information light obtained from the irradiated particle;
wherein at least one of said first and second detecting apparatuses includes one or more fiber optics, of which one ends are arranged adjacent the flow oath so as to collect the information light;
wherein the flow path defined by said path-defining structure has a rectangular cross section defined by a pair of first walls and a pair of second walls perpendicular to the first walls;
wherein said irradiation apparatus emits light to one of the first walls;
wherein said first detecting apparatus detects light transmitting through another one of the first walls;
wherein said second detecting apparatus detects light transmitting through one of the second walls;
wherein said path-defining structure includes a partition plate between one ends of the fiber optics and one of the walls opposing to one ends of the fiber optics; and
wherein one ends of the fiber optics opposes to the partition plate.

12. The system according to claim 11,
wherein a gap between one ends of the fiber optics and the partition plate is filled up with transparent filler material.

13. The system according to claim 11,
wherein a gap between one ends of the fiber optics and the partition plate is filled up with transparent filler material having refraction index that is substantially intermediate between ones of the fiber optics and the partition plate.

14. A system for collecting biological information on a dyed biological particle by irradiating light onto liquid containing the dyed biological particles and detecting information light therefrom, the system comprising:
a path-defining structure of transparent material for defining a flow path through which liquid containing the dyed biological particles runs;
an irradiation apparatus for irradiating light onto the particles passing through the flow path;
a first detecting apparatus for detecting first information light obtained from the irradiated particle; and
a second detecting apparatus for detecting second information light obtained from the irradiated particle;
wherein said irradiation apparatus includes first optical elements for collecting light at a first position and second optical elements for collecting light at a second position, the first and second positions being spaced from each other by a predetermined distance along a central axis of the flow path;
wherein at least one of said first and second detecting apparatuses includes first and second fiber optics, of which one ends are arranged adjacent the flow path so as to collect the information light from the particles irradiated at the first and second positions.

15. The system according to claim 14,
wherein the first and second positions are determined such that the emitted/scattered light from the particle at the first position is prevented from entering into the second fiber optics, and the scattered light from the particle at the second position is prevented from entering into the first fiber optics.

16. The system according to claim 14,
wherein a fiber bundle is formed by a central fiber optics and six fiber optics that are closely arranged around the central fiber optics; and
wherein two of the fiber optics of the fiber bundle are selectively used as the first and second fiber optics.

17. A system for collecting biological information on a dyed biological particle by irradiating light onto liquid containing the dyed biological particles and detecting information light therefrom, the system comprising:
a path-defining structure of transparent material defining a flow path through which the liquid containing the dyed biological particles runs;
an irradiation apparatus for irradiating light onto the particles passing through the flow path;
a first detecting apparatus for detecting first information light obtained from the irradiated particle; and
a second detecting apparatus for detecting second information light obtained from the irradiated particle;
wherein at least one of said first and second detecting apparatuses includes one or more fiber optics, of which one ends are arranged adjacent the flow oath so as to collect the information light;
wherein at least one of said first and second detecting apparatus includes a spectrometer for splitting light components from light received by the fiber optics, and a plurality of optical detectors for reading information within the light split by the spectrometer;
a signal processing apparatus;
wherein the signal processing apparatus includes an A/W/H circuitry for calculating an area, width, and height of a plurality of analog signals output from a plurality of the optical detectors,
an A/D converter for converting analog signals output from the A/W/H circuitry into digital signals, a first-in first-out memory for storing digital information based upon digital signals output the A/D converter and for simultaneously outputting a plurality of digital information, a compensation circuitry for compensating digital signals output from the memory, and a logarithmic calculator for logarithmically calculating digital information output from the compensation circuitry.

18. A system for collecting biological information on a dyed biological particle by irradiating light onto liquid containing the dyed biological particles and detecting information light therefrom, the system comprising:

a path-defining structure of transparent material defining a flow path through which the liquid containing the dyed biological particles runs;

an irradiation apparatus for irradiating light onto the particles passing through the flow path;

a first detecting apparatus for detecting first information light obtained from the irradiated particle;

a second detecting apparatus for detecting second information light obtained from the irradiated particle;

wherein at least one of said first and second detecting apparatuses includes one or more fiber optics, of which one ends are arranged adjacent the flow path so as to collect the information light;

a cylindrical container having a laminar-flow generating chamber provided upstream the flow path;

a sheath-fluid line for supplying sheath fluid constituting a main body of the liquid from an upper end of the cylindrical container;

a suspension-fluid tube arranged along the central axis of the cylindrical container for supplying suspension fluid containing the particles into the sheath fluid running within the laminar-flow generating chamber;

a mechanism for adjusting a position of a suspension-fluid outlet of the suspension-fluid tube; and a drain line connected with a lower end of the laminar-flow generating chamber;

a sheath-fluid source of the sheath fluid;

a sheath-fluid waste of the sheath fluid;

means for selectively connecting the drain line with either one of the sheath-fluid source and the sheath-fluid waste.

19. A system for collecting biological information on a dyed biological particle by irradiating light onto liquid containing the dyed biological particles and detecting information light therefrom, the system comprising:

a path-defining structure of transparent material defining a flow path through which the liquid containing the dyed biological particles runs;

an irradiation apparatus for irradiating light onto the particles passing through the flow path;

a first detecting apparatus for detecting first information light obtained from the irradiated particle;

a second detecting apparatus for detecting second information light obtained from the irradiated particle;

wherein at least one of said first and second detecting apparatuses includes one or more fiber optics, of which one ends are arranged adjacent the flow path so as to collect the information light;

charging means for charging a droplet injected from the flow path;

a pair of deflecting plates provided adjacent a dropping path of the charged droplet; and a power source circuitry for generating an electrical field between a pair of the deflecting plates;

wherein at least one of the deflecting plates is formed from a porous plate, and an aspirator being provided at rear end of the porous deflecting plate for aspirating droplet attached on the porous deflecting plate.

* * * * *